US006811536B2

(12) United States Patent
Sun et al.

(10) Patent No.: US 6,811,536 B2
(45) Date of Patent: Nov. 2, 2004

(54) NON-INVASIVE APPARATUS SYSTEM FOR MONITORING AUTONOMIC NERVOUS SYSTEM AND USES THEREOF

(75) Inventors: Dehchuan Sun, Taipei (TW); Terry B. J. Kuo, Hualian (TW)

(73) Assignee: Industrial Technology Research Institute, Chutung (TW)

( * ) Notice: Subject to any disclaimer, the term of this patent is extended or adjusted under 35 U.S.C. 154(b) by 87 days.

(21) Appl. No.: 10/244,309

(22) Filed: Sep. 16, 2002

(65) Prior Publication Data

US 2004/0054292 A1 Mar. 18, 2004

(30) Foreign Application Priority Data

Apr. 1, 2002 (CN) ........................................ 91106492 A (51) Int. Cl.$^7$ .............................. A61B 5/02; A61B 5/04
(52) U.S. Cl. ........................ 600/500; 600/509; 600/485
(58) Field of Search ................................. 600/500–509, 600/481, 485, 486

(56) References Cited

U.S. PATENT DOCUMENTS 4,078,551 A * 3/1978 Wohltjen et al. ............ 600/494
6,050,951 A * 4/2000 Friedman et al. ........... 600/485

FOREIGN PATENT DOCUMENTS

TW 363404 12/1987
WO 02051307 7/2002

OTHER PUBLICATIONS

Database Biosis Online, Biosciences Information Services, (Apl. 1999), Abstract. Scheinin, H. et al. "Spectral Analysis of heart rate variability as a quantitative measure of para-sympatholytic effect—Integrated pharmacokinetics and pharmadynamics of three anticholinergic drugs". *Therapeutic Drug Monitoring*, (Apr. 1999), 21(2): 141–151.

Database Biosis Online, Biosciences Information Services, (1993), Abstract. Kuo, T. et al. "Continuous, on–line, real–time spectral analysis of systemic arterial pressure signals". *American Journal of Physiology*, (1993), 264(6) part 2: pp. H2208–H2213.

Task Force of the European Society of Cardiology and the North American Society of Pacing and Electrophysiology, "Heart Rate Variability: Standards of Measurement, Physiological Interpretation, and Clinical Use". *Circulation*, (1996), 93: 1043–1065.

Kuo, T.B. et al. "Effect of aging on gender differences in neural control of heart rate", *American Journal of Physiology*, (Dec. 1999), vol. 277, No. 6, part 2: pp. H2233–H2239.

M. Malik, "Heart Rate Variability: Standards of Measurement, Physiological Interpretation, and Clinical Use" *Circulation*, vol. 93, No. 5, p. 1043–1065 (1996).

T.B.J. Kuo, et al. "Effect of aging on gender differences in neural control of heart rate" *Am. J. Physiol.*, vol. 277: H2233–H2239, (1999).

M.W. Yang, et al. "Continuous, on–line, real–time spectral analysis of SAP signals during cardiopulmonary bypass" *Am. J. Physiol.*, vol. 268: H2329–H2335, (1995).

T.B.J. Kuo, et al. "Continuous, on–line, real–time spectral analysis of systemic arterial pressure signals" *Am. J. Physiol.*, vol. 264: H2208–H2213, (1993).

(List continued on next page.)

*Primary Examiner*—Mary Beth Jones
*Assistant Examiner*—Navin Natnithithadha
(74) *Attorney, Agent, or Firm*—Ladas & Parry (57) ABSTRACT

A non-invasive apparatus system for monitoring autonomic nervous system, and its uses in monitoring autonomic nervous system functional change side effects caused by drugs and monitoring the aging of autonomic nervous system and tracing therapeutic effect thereof.

11 Claims, 8 Drawing Sheets

OTHER PUBLICATIONS

A. Malliani, et al. "Cardiovascular Neural Regulation Explored in the Frequency Domain" *Circulation*, vol. 84, No. 2, 482–492, (1991).

R.W. DeBoer, et al. "Hemodynamic fluctuations and baroreflex sensitivity in humans: a beat–to–beat model" *Am. J. Physiol.*, vol. 253: H680–H689, (1987).

S. Akselrod, et al. "Power Spectrum Analysis of Heart Rate Fluctuation: A Quantitative Probe of Beat–to–Beat Cardiovascular Control" *Science*, vol. 213, p. 220–223, (1981).

S. Akselrod, "Spectral analysis of fluctuations in cardiovascular parameters: a quantitative tool for the investigation of autonomic control" TIPS, vol. 9, p. 6–9, (1988).

* cited by examiner

NON-INVASIVE APPARATUS SYSTEM FOR MONITORING AUTONOMIC NERVOUS SYSTEM AND USES THEREOF

FIELD OF THE INVENTION

The present invention relates to a non-invasive apparatus system for non-invasively monitoring autonomic nervous system and the use thereof in monitoring autonomic nervous system functional change side effects, which are caused by drugs or aging of autonomic nervous system, and the methods for tracing therapeutic effect by using the same.

BACKGROUNDS OF THE INVENTION

In view of the world population having the tendency of aging and the increasing population suffering from chronic diseases caused by aging, the pharmaceutical companies around the world have been developing new drugs for treating the chronic diseases to improve life qualities. However, in addition to the desired activities, many drugs being or to be marketed are usually accompanied with several side effects, including the influences to autonomic nerves (sympathetic and parasympathetic nerves). Autonomic nerves control several important conscious and unconscious activities in human, such as heart rate, blood pressure, blood sugar, sleeping, sweating, bowel peristalsis, and bronchodilation. Therefore, if a drug has any harmful inference, it may cause severe diseases (e.g. hypertension or arrhythmia) or abnormality (e.g. insomnia or unregulated body temperature), and the physical and mental health of the patients will be affected. This type of cases has been commonly described in clinical articles and market reports. For example, as reported in American Associated Press (25 Aug. 2001), GlaxoSmithKline PLC, a pharmaceutical company in the United Kingdom, was accused by a group of American patients for the reason that its drug Paxil, for treating depression may cause side effects to sympathetic and central nervous system, which include causing seizure, night sweating, and suicidal thought. Although pharmaceutical companies and doctors have been aware of the side effects on autonomic nerves, there is currently no effective means to resolve the problems of side effects caused by drugs. Furthermore, no methods and techniques for directly monitoring these side effects are available.

Nowadays, in the duration of developing new drugs, all pharmaceutical companies in the world measure the nervous toxicity of the new drugs by animal models. Normally, only the drugs having low toxicity can enter the clinical trial stage. During the human clinical trials, doctors can merely investigate orally or by questionnaire to determine whether the drug influences the normal functions of the autonomic nervous system, such as the appearance of the syndromes of insomnia, blushing, palpitation, and dizziness, and by associating with measurement of blood pressure and heart rate to determine the patient's responses of autonomic nervous system. However, in many cases, acute or chronic side effects of drugs are caused or amplified by drug-drug interactions resulting from several drugs being taken by the patients simultaneously. It is impossible to test all combinations of drugs during the clinical trials, so that the problems caused by side effects happen again and again.

Additionally, according to the experiences of the clinical trials, the acute and severe side effects only happen to a very low percentage (usually smaller than 0.1%) of patients taking medicines. Therefore, according to the statistics, an acute and severe side effect to autonomic nervous system will not be found in a clinical trial of less than one thousand patients. Even in a clinical trail of ten thousand patients (few pharmaceutical companies would hold a clinical trial in such a large scale), only about ten severe cases would happen. In light of the special case having a probability of less than 1%, it is classified as an "unknown reason" in general clinical trial reports and the data is removed from the normal analysis range. Consequently, the process of marketing the drug will continue without being hindered by the special cases. However, after a new drug is marketed, the cases of acute side effects increase suddenly (more than hundreds of people) because more than one million people are taking the drug. Under these circumstances, governmental health authorities, pharmaceutical companies and doctors may feel panicky about these cases and decide to withdraw the drug from the market. In 1997, American Home Product stopped selling a drug, Fen-Phen, intended for weight control, which has been approved for marketing by the U.S. Food and Drug Administration (FDA) in 1996 and had been taken by more than six million of people all over the world, for the reasons that the drug may severely damage heart valves and nervous system. The company was decided to pay a compensation of twenty seven million U.S. dollars to an American woman, and in a following class lawsuit, the estimated compensation is expected to be more than one billion U.S. dollars. Evidently, side effects and withdrawal of drugs will not only cause a loss of revenue profit but also a great deal of compensation in law suits.

In addition, oral or questionary investigations for tracing the influences of drugs in the outpatient department or clinic are not frequent enough to prevent acute side effects. Furthermore, patients (especially elder patients) usually incorrectly recognize or remember the syndromes caused by the autonomic nervous system (e.g. whether night sweating, accelerating heart rate, or dizziness really has happened or not). Therefore, the cases caused by side effects happen frequently.

In another aspect, various anti-aging drugs or treatment have been gradually developed with the aging population. Some doctors consider that aging process can be delayed and even the aged tissues can be rejuvenated by suitable treatments. Usually, the doctor would ask the patient to conduct a series of tests first to estimate the degree of aging. For example, if the amounts of growth hormone and sex hormone in the blood of a patient are lower than those of normal persons at the same age, this indicates that the patient's "physiological age" is older than his or her "chronological or actual age". Doctors also use other physical methods to test the patient's physiological functions. For example, the doctor allows the patient to lie down for a while and then asks the patient to stand suddenly to observe whether the patient will feel dizzy or can stand stably; or the doctor holds a small piece of paper (or dollar bill) and then releases it suddenly to observe whether the fingers of the patient awaiting below the paper can catch the paper fast enough. The phenomenon of dizziness is associate with a sudden change of blood pressure, which is regulated by autonomic nerve in human, and the test of catching a small piece of paper is associated with the brain function, nerve transmission and muscle contraction. However, these tests and other physical tests can only be used for qualitative evaluation, but not for quantitative determination. Doctors often prescribe drugs (e.g. hormones), physical treatments or nutrition supplements, or recommend increasing exercise to help their patients to delay aging and even to rejuvenate. However, these treating methods need a simple and quantitative assay method to trace the therapeutic effect. According to the published articles, no methods or apparatus systems have been found to be able to use heart rate variability or the similar information as the indicator of aging.

Therefore, a non-invasively and easily operative method and apparatus system for monitoring the functions of autonomic nervous system and for quantifying the aging physiological statuses are needed to avoid acute side effects and to help doctors in diagnosing the aging condition and tracing the treatment of aging.

Recently, Task Force of the European Society of Cardiology and the North American Society of Pacing and Electrophysiology (Heart Rate Variability: Standards of Measurement, Physiological Interpretation and Clinical Use; Circulation 93:1043–1065; 1996) and Malliani et al. (Cardiovascular Neural Regulation Explored in the Frequency Domain; Circulation 84: 482–492; 1991) found that heart rate variability not only is affected by the undulation of respiratory, but also indicates the functions of the autonomic nervous system. The heart rate variability is related to the minute, cyclic change of heartbeat (i.e. heart rate). While heartbeat is normally maintained at 60–90 times per minute at rest, some regular or irregular oscillations have been found within the pulse data. These oscillations are very small, so that they cannot be accurately analyzed by the traditional analytical methods. Using the modern technologies of computer and spectral analysis, Akselrod et al (Power Spectrum Analysis of Heart Rate Fluctuation: A Quantitative Probe of Beat-to-Beat Cardiovascular Control; Science; 213:220–222; 1981 and Spectral Analysis of Fluctuations in Cardiovascular Parameters: A Quantitative Tool for the Investigation of Autonomic Control; Trends in Pharmacological Science; 9:6–9; 1988) and Kuo et al (Continuous, On-line, Real-time Spectral Analysis of Arterial Blood Pressure Using a Personal Computer; American Journal of Physiology; 264:H2208–H2213; 1993) discovered microoscillations in heart rate variability through the spectral analysis. They found that the micro-oscillations in heart rate variability can generally be divided into two groups: a high frequency (HF) variability and a low frequency (LF) variability. The low frequency variability can further be divided into a very low frequency variability and a low frequency variability. By way of animal and human tests, De Boer et al (Hemodynamic Fluctuations and Baroreflex Sensitivity in Humans: A Beat-to-Beat Model: American Journal of Physiology; 253:H680–H689; 1987) proved that the variance in heart rate variability, the total power (TP) and the high frequency (HF) are associated with the activity of parasympathetic nerves, and the ratio of low frequency variability to high frequency variability (LF/HF) and the percentage of low frequency variability (LF%) are associated with the activity of sympathetic nerves.

Many different methods can be used for measuring heart rate and variability thereof. Two methods are most commonly used. One is measuring patient's artery pressure signal, which can be conducted invasively (by implanting a pressure sensor into the artery of human body) or non-invasively (by placing a pressure sensor on the skin surface near the artery); and the other is placing electrodes on patient's chest to measure the electrocardiographic signal. The signals obtained from the methods can be converted into heart rate (HR). The heart rate is the reciprocal of the intervals between the peaks of the signals of the measured blood pressure or electrocardiograph. The micro oscillations of heart rate can be converted to spectrum by the Fourier Transform method and then further be divided into high frequency, low frequency and very low frequency variability according to their definitions. Based on the 2D Power Spectrum Density-Frequency graph, the power of each variability can be obtained by integrating the corresponding range of the frequency. Yang et al (Continuous, On-line, Real-Time Spectral Analysis of SAP Signals During Cardiopulmonary Bypass; American Journal of Physiology; 268:H2329–H2335; 1995) defined the human frequency ranges to be high frequency of 0.15–0.40 Hz, low frequency of 0.04–0.15 Hz and very low frequency of 0.003–0.04 Hz.

ROC (Taiwan) Patent Publication No. 363,404 discloses a heart rate variability analyzing electrocardiograph converter (with electrodes) for measuring the electric potential signal of heart contraction, wherein the heart rate variability is calculated from the signal by the Fourier Transform method and spectral analysis. However, the invention is to provide a novel heart rate variability analyzing electrocardiograph converter, which is characterized by the designation of new software and hardware, and the apparatus system containing the same.

The uses of monitoring the side effects to the autonomic nervous system caused by drugs, and measuring the "physiological age" have neither been disclosed nor suggested in the prior art mentioned above.

The subject of the invention provides an apparatus system and a method which can discover and monitor the side effects to the autonomic nervous system caused by drugs at anytime, and can provide warning at the early stage to avoid severe side effects. The apparatus system and method of the present invention can also be used for tracing aging of autonomic nervous system by monitoring the activity of the autonomic nervous system.

SUMMARY OF THE INVENTION

The present invention provides a non-invasive apparatus system for monitoring the side effects to the autonomic nervous system caused by drugs to prevent acute or chronic side effects to the brain nerves; and for monitoring the aging of nervous system by measuring the "physiological age" of the patient based on the activity of the autonomic nervous system.

DETAILED DESCRIPTION OF THE INVENTION

The present invention relates to an apparatus system for measuring autonomic nervous system by using non-invasive techniques, which comprises (a) a sensor for measuring artery sphygmograms or heart potential signals to form electric waves representing the artery sphygmograms or heart potential signals; and (b) an analyzer for receiving the electric waves from (a), wherein heart rate variability parameters in the electric waves can be calculated by Fourier Transform or Fast Fourier Transform and spectral analysis.

Autonomic nervous system comprises a sympathetic nervous system and a parasympathetic nervous system, wherein the effects of sympathetic stimulation include elevation of blood pressure, increase of heart rate, contraction of blood vessel, dilation of pupil, increase of sweating, increase of blood sugar, contraction of skin, lowering of bowel peristalsis, and increase of metabolism; often in opposite functions, the parasympathetic stimulation causes lowing of blood pressure, decrease of heart rate, dilation of blood vessel, contraction of pupil, contraction of pulmonary, decrease of blood sugar, increase of bowel peristalsis, and lowering of metabolism. If the functions of the autonomic nervous system are changed by drugs or by the aging of nervous system, the symptoms of hypertension, hypotension, arrhythmia, insomnia, unregulated body temperature, flushing, dizziness, or sweating will appear.

According to the present invention, the sensors can be, but are not limited to, a pressure sensing device or an electrode chip. The pressure sensing device can be any conventional sensor for use in measuring sphygmogram, such as a pressure sensor or a strain gauge. The sensing device can be placed on the skin surface near artery, such as the positions of head, neck, finger, wrist, forearm, buttocks, shoulder, thigh, leg, and foot. It is preferable that the pressure sensing device is an apparatus worn on wrist to measure the blood pressure waveform or sphygmogram of radial artery. The electrode can be placed in one or more on the skin surface near the heart to measure the heart potential.

According to the present invention, the analyzers can use any conventional methods, such as those disclosed by De Boer et al. (1987), Yang et al. (1995) and ROC (Taiwan) Patent Publication No. 363,404, to convert the sphygmogram or heart potential measured by the sensor into a spectrum by the Fourier Transform method or the Fast Fourier Transform method, and can use spectral analysis to calculate the heart rate variability parameters from the spectrum.

According to the invention, the heart rate variability parameters comprise the parameters listed in Table 1:

TABLE 1

| Parameter | Unit | Definition | Associations with Autonomic Nervous System |
|---|---|---|---|
| Heart Rate Period | ms | Heart rate period is a time period betweem R peaks in the QRS wave complex in the electrocardiogram (ECG) or the time period between the first major peaks in the sphygmogram. | The increase of heart rate period represents the decrease of the heart rate and the increase of the activities of parasympathetic nerve system. |
| Variance | $ms^2$ | Variance is a statistical variance of the values of the intervals between the R peaks in ECG or between the first major peaks in the sphygmogram during the testing period. | Variance represents the functions and activities of para-sympathetic nervous system. |

TABLE 1-continued

| Parameter | Unit | Definition | Associations with Autonomic Nervous System |
|---|---|---|---|
| Total Power (TP) | $ms^2$ | Total power is a power measured in all spectral ranges, which is obtained by integrating all spectral ranges in the power spectrum density-frequency graph. | Total power represents the functions and activities of parasympathetic nervous system. |
| Very Low Frequency (VLF) | $ms^2$ | VLF is a power in the spectral range of very low frequency (generally defined as between 0.003~0.04 Hz in human) | — |
| Low Frequency (LF) | $ms^2$ | LF is a power in the spectral range of low frequency (generally defined as between 0.04~0.15 Hz in human) | LF represents the integrated index of the functions and activities of sympathetic and para-sympathetic nervous systems. |
| High Frequency (HF) | $ms^2$ | HF is a power in the spectral range of high frequency (generally defined as between 0.15~0.4 Hz in human) | HF represents the functions and activities of para-sympathetic nervous system. |
| Low Frequency/High Frequency (LF/HF) | ratio | $LF(ms^2)/HF(ms^2)$ | LF/HF represents the functions and activities of sympathetic nervous system. |
| Percentage of Low Frequency (LF %) | % | LF/(TP − VLF)*100 | LF % represents the functions and activities of sympathetic nervous system. |
| Percentage of High Frequency (HF %) | % | HF/(TP − VLF)*100 | — |

***First major peak in the sphygmogram depicts the largest peak in the blood pressure waveform caused by rapid ejection of blood from left ventricle.

According to the present invention, the analyzer can be, but is not limited to, a micro computer or an oscilloscope containing software and hardware elements, which can receive, storage, analyze, and show the sphygmograms or electrocardiographs obtained from the sensors.

According to the present invention, the analyzer further comprises a display device to show the data and results recorded in the analyzer. The display device can be, but is not limited to, a liquid crystal display device, an oscilloscope, a digital light-emitting diode, a cathode-ray tube, or a printer.

According to the present invention, the analyzer further comprises an apparatus which can transfer the measured and analyzed data to a terminal at hospital's or doctor's end. In addition, the apparatus further comprises a signal delivering mean for receiving signals transferred from the hospital or doctor. The signal delivering means can transfer signals by a wired or wireless way. The signals can be transferred by, for example, telephone, network satellite and wireless communication.

According to the present invention, the analyzer optionally comprises a warning device which can emit warning signals. The warning signal can be a sound or light signal. The warning device can emit the warning signal based on the results obtained from the analyzer or the signal transferred from the hospital or by the doctor. The warning device can, but is not limited to, generate sound, show words or graphs by the display device, or show twinkle lights.

The present invention further provides a method for monitoring the side effects of the functional changes to the autonomic nervous system caused by drugs, which comprises the utilization of the apparatus system of the invention to monitor and calculate the heart rate variability parameters is before and after the drug is taken. If the value of change, before or after the drug is taken, in one or more heart rate variability parameters is smaller than a predetermined value, it represents that the drug does not cause an autonomic nervous system side effect. If the value of change in one or more heart rate variability parameters falls between two predetermined values, it represents that the drug has induced a certain degree of functional change to the autonomic nervous system. If the value of change in one or more heart rate variability parameters is larger than a predetermined value, it represents that the drug has induced a severe functional change to the autonomic nervous system.

According to the preferred embodiment of the present invention, the side effects of the functional change to the autonomic nervous system caused by drugs in a patient can be efficiently monitored and prevented by the following steps:

(I) periodically measuring the heart rate variability parameters of the patient before and during the drug administration, wherein the periodical measurement can be proceeded daily, weekly or in any other special period;

(II) calculating the degree of the functional change to the autonomic nervous system induced by taking the drug based on the data obtained from step (I), wherein the change comprises a variation comprising high frequency, low frequency and very low frequency of the heart rate variability parameters as listed in Table 1, before and after taking the drug; and (III) classifying the data from step (II) into one of the following three types, which are defined based on the clinical trial data:

(a) the data being lower than a specific value represents that the drug is function normally;

(b) the data falling between two specific values represents that the drug has induced a functional change to the autonomic nervous system, the occurrence of the functional change needs to be strictly monitored, and a warning should be sent to the patient and/or the doctor; and (c) the data being higher than a specific value represents that a functional change to the autonomic nervous system induced by the drug has affected the patient's health and the drug should be stop taken immediately.

Figure 1:
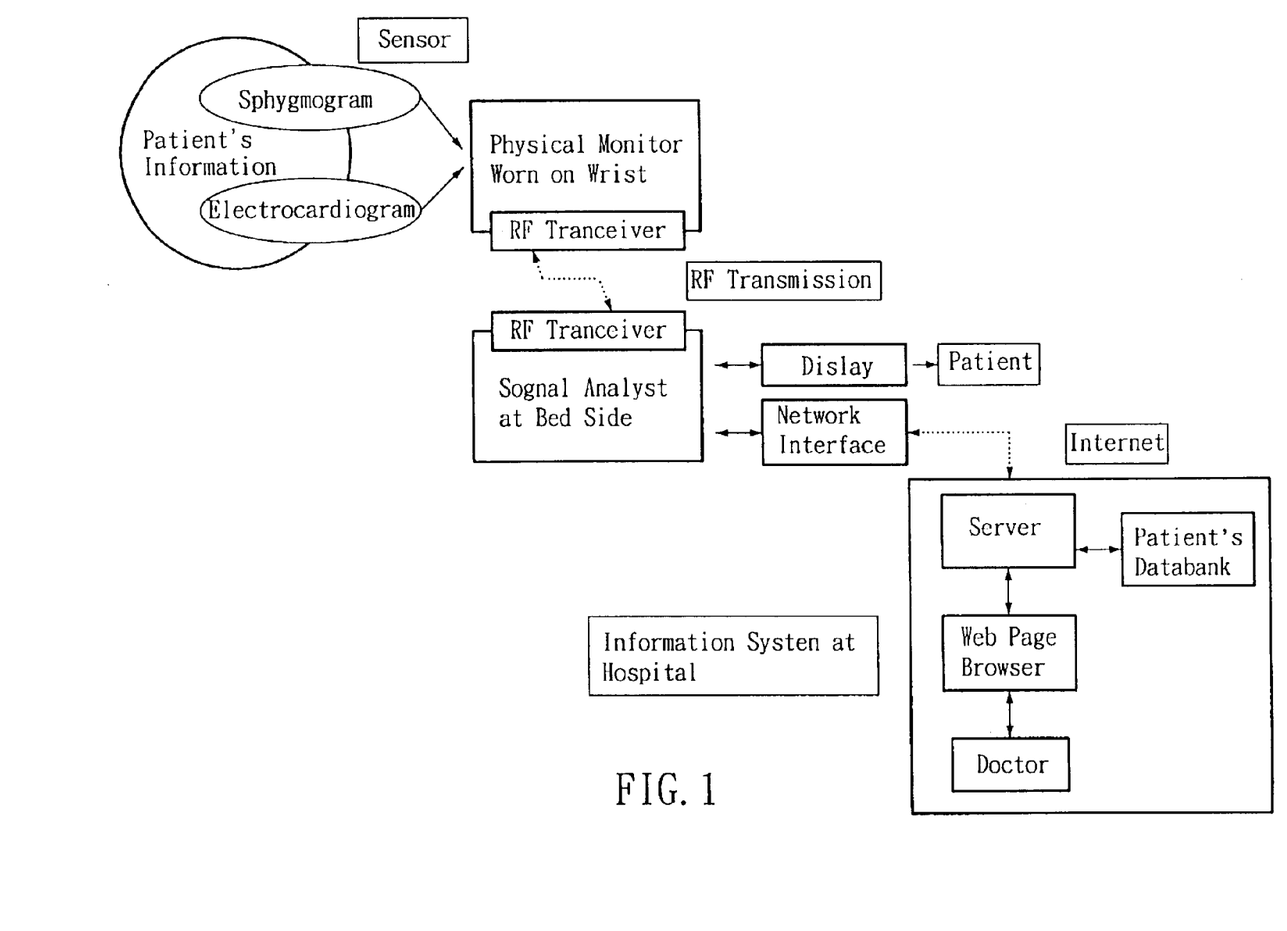
FIG. 1 illustrates a preferred embodiment of the invention.

According to another preferred embodiment of the present invention, the method and apparatus system are provided for persons to use at home, and the patients can be monitored every day continuously. The data obtained can be transferred to the doctor by the signal delivering mean in the analyzer to inform the doctor of the patient's condition, and therefore a further treatment to the patient can be taken, if necessary. For example, as shown in FIG. 1, a wrist type sphygmomanometer using a pressure sensor transforms the patient's arterial radials sphygmogram to an electric wave. After the electric wave is amplified, filtered and analogy-digital transformed, it is delivered to a bedside analyzer. Said analyzer comprises a micro computer for recording the sphygmogram and analyzing heart rate variability. The data will be shown by the displaying device of the analyzer and be transferred to the patient's information server or the terminal at the hospital or clinic. The server or terminal will record, analyze and compare the data transferred from the patient's end, and will transfer the doctor's instructions to the bedside analyzer at the patient's end.

The present invention further provides a method for monitoring the aging of autonomic nervous system and tracing the therapeutic effect thereof, which comprises the utilization of the apparatus system of the present invention to monitor and calculate the heart rate variability parameters; and the comparison of the parameters with those of normal people at the same age and of the same sex to determine the degree of aging of autonomic nervous system, and thereby to trace the therapeutic effect to aging.

According to a preferred embodiment of the invention, the degree of aging of autonomic nervous system and the tracing of therapeutic effect to aging can be determined and proceeded by the following steps:

(I) choosing a group of healthy people, both males and females, at various ages in the number with statistical meaning, and using the apparatus system of the invention to calculate each person's heart rate variability parameters;

(II) dividing the heart rate variability parameters obtained from Step (I) into a male group and a female group, graphing their/the individuals' parameters versus their ages, and using statistic curve smoothing method to calculate the means and standard deviations at each age point on the curve of the graphs; and (III) obtaining the heart rate variability parameters of the patients under diagnosis by the method of Step (I), and comparing the parameters, based on the age and sex of the patient, with the means and standard deviations of the parameters of the healthy individuals obtained from the curve of Step (II); if a difference of any heart rate variability parameters between the patient and the normal people is larger than one standard deviation range of the parameter or other given value, the patient is determined as abnormal; otherwise is determined as normal; or (IV) obtaining the heart rate variability parameters of the patient, who is receiving an anti-aging treatment, by the method of Step (I) periodically, and comparing the parameters with those of normal people by the method of Step (III); if the differences decrease with the treatment, the treatment is determined effective; otherwise it is determined as ineffective; and, optionally, the results obtained during the treatment can be compared with those before the treatment to determine whether the condition of the patient is stable, better or worse.

The following examples are provided for illustration, but not for limiting the invention.

EXAMPLE 1
Monitoring Autonomic Nervous System Functional Change Side Effects Caused by Drugs in Rats Matured male Sprague-Dawley rats (weighed 250–350 g) were first sensitizing anesthetized by intraperitoneal injecting of pentobarbital sodium (50 mg/kg) and then were general anesthetized by continuously infusion with pentobarbital sodium (15 mg/kg). The rats were intubated in both femoral veins, wherein one was used for continuously dropping anesthesia and the other was used for delivering testing drug. The rates were tracheal intubated to connect with a respirator (Havard 683) for mechanical respiration. In addition, the skeletal muscle of the whole body of the animals was anesthetized by administrating pancuronium. In order to record the artery pressure, the intubation at the right femoral artery was linked to a PE-50 tube connected with a syringe pre-filled with heparinized saline (200 unit/mL). The artery pressure and heart rate were recorded by a pressure sensory machine (1290C, Hewlett-Packard) in the tube. The artery pressure was converted by a pressure converter (Statham, P23ID, frequency range: DC to 200 Hz), amplified by a pre-amplifier (Gould, G-13-4615-52), and then filtered (DC to 100 Hz). Electrocardiograph signal was recorded by a second guided electrocardiograph recorder. The signal was amplified by a pre-amplifier(Gould G-20-4615-58) and then filtered (3–300 Hz). At the same time, the signal and the artery pressure were caught by a 12 bit analog-digital converter in an analyzing computer in a frequency of 256 points per second in every channel. The computer used was an IBM-PC compatible type comprising an Intel 80486 micro processor and a 4 MB memory. The Heart rate signals (digital blood pressure signal or electrocardiograph signal) were simultaneously and continuously on-line analyzed by the Fast Fourier Transform method, and the power of each special frequency interval was quantified by integration. High frequency (frequency between 0.5 to 2.4 Hz) in spectrum was considered as an index of parasympathetic nervous function, low frequency % [=100× low frequency/(high frequency+low frequency)] was considered as an index of sympathetic nervous function, and the means of heart rate period and variance were considered as references.

The rats were divided into three groups, and each group had 4 to 6 animals. A group of animals were intravenously administered with yohimbine (1 mg/kg), which is a central nervous system $\alpha_2$ receptor antagonist being able to stimulate sympathetic nervous functions and inhibit parasympathetic nervous functions. Another group of animals was intravenously administered with guanabenz (100 $\mu$g/kg), which is a central nervous system $\alpha_2$ receptor agonist being able to inhibit sympathetic nervous functions and stimulate parasympathetic nervous functions. The animals administered with saline of the same volume was classified as a controlled group.

Figure 2:
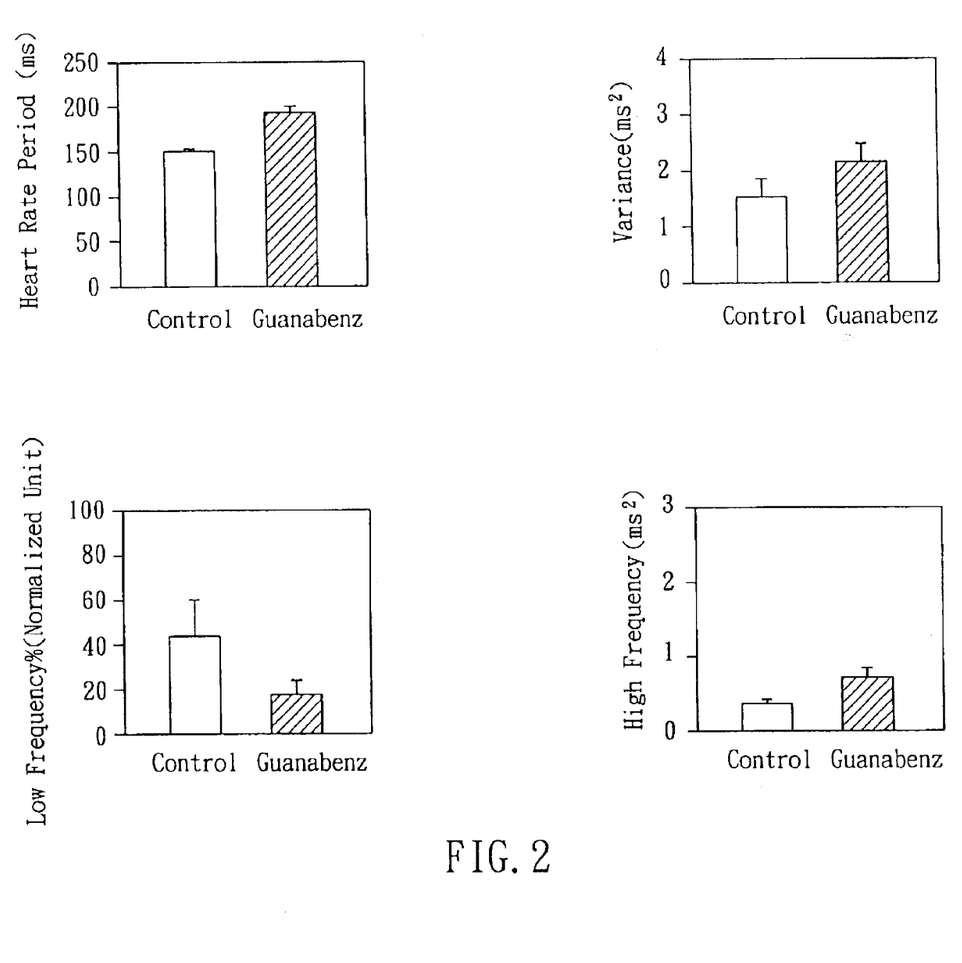
FIG. 2 illustrates the heart rate variability parameters of the rats after being treated with guanabenz.
Figure 3:
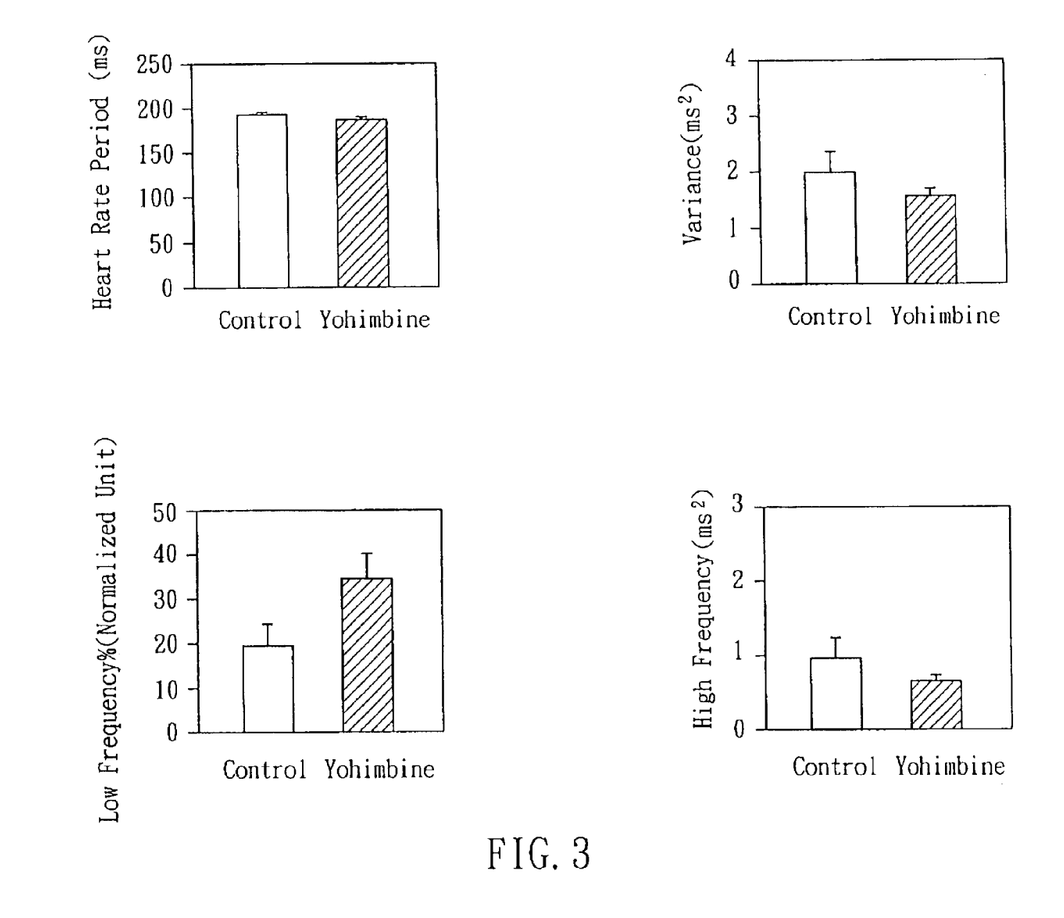
FIG. 3 illustrates the changes of the heart rate variability parameters of the rats after being treated with yohimbine.

Prior to applying the drugs, basal blood pressure, mean value of heart rate period and spectral analysis were measured for about 10 minutes, and after the drugs being intravenously administered, the effects of the drugs were measured for 30 minutes. FIG. 2 shows that guanabenz increased the heart rate period, heart rate variability and high frequency, and tremendously lowered the low frequency %, for the known effects that guanabenz can inhibit the sympathetic nervous activity and stimulate the parasympathetic nervous activity. Therefore, low frequency % is shown to be a valid index of the sympathetic nervous activity, and high frequency an index of the parasympathetic nervous activity, respectively. FIG. 3 shows that yohimbine, on the contrary, tremendously increased low frequency % and lowered heart rate period and high frequency, for the known effects that yohimbine can increase the sympathetic nervous activity and inhibit the parasympathetic nervous activity. Therefore, low frequency % is shown to be a valid index of sympathetic nervous activity and high frequency an index of parasympathetic nervous activity, respectively.

Figure 4:
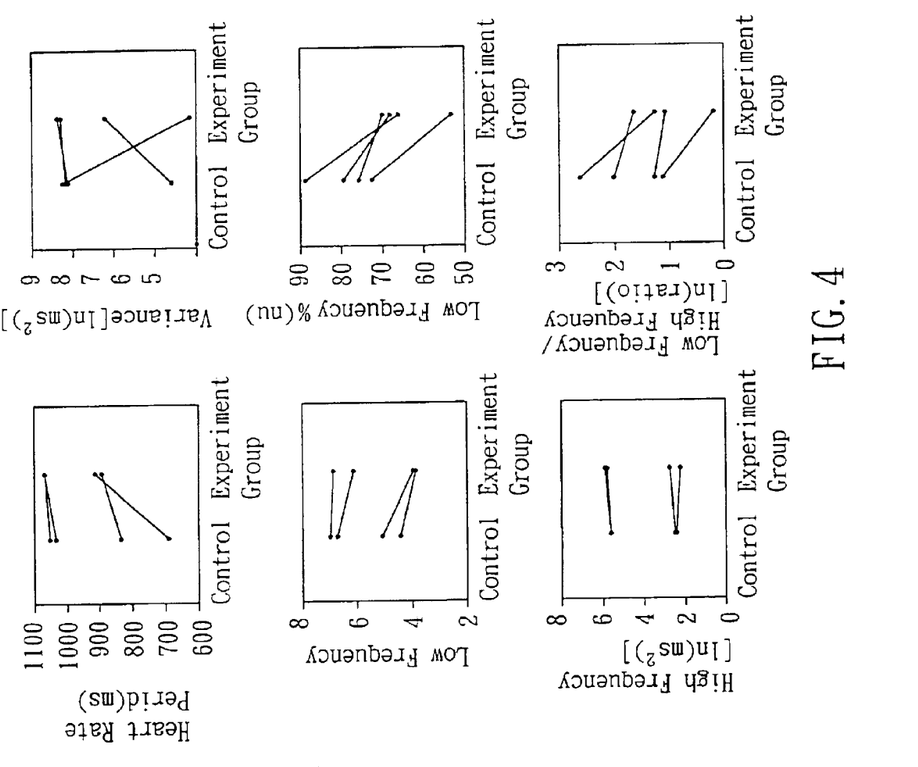
FIG. 4 illustrates the changes the heart rate variability parameters of the patients after being treated with a hypotensive drug.
Figure 5:
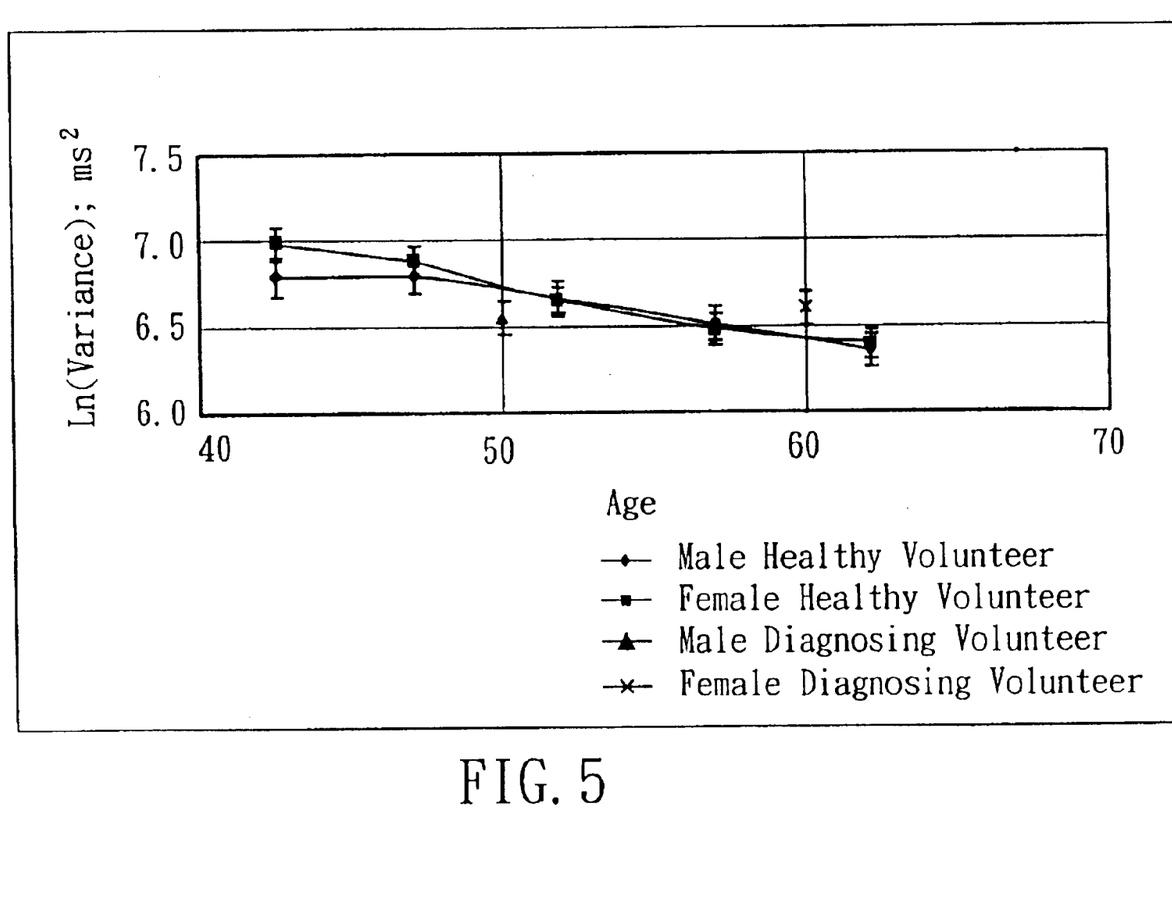
FIG. 5 illustrates the relations between the variability and the age of the control group and the experiment group.
Figure 6:
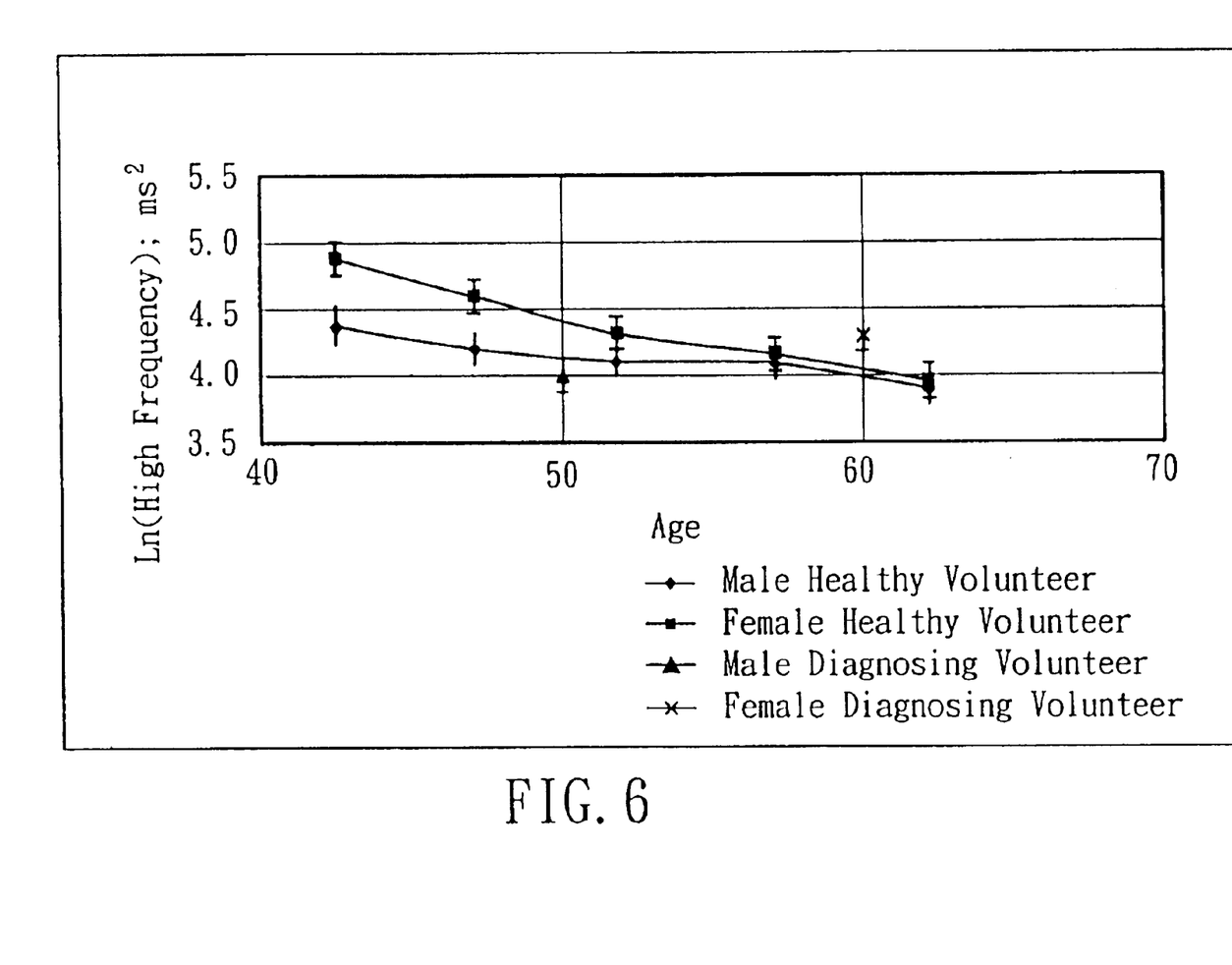
FIG. 6 illustrates the relations between the high frequency variability and the age of the control group and the experiment group.
Figure 7:
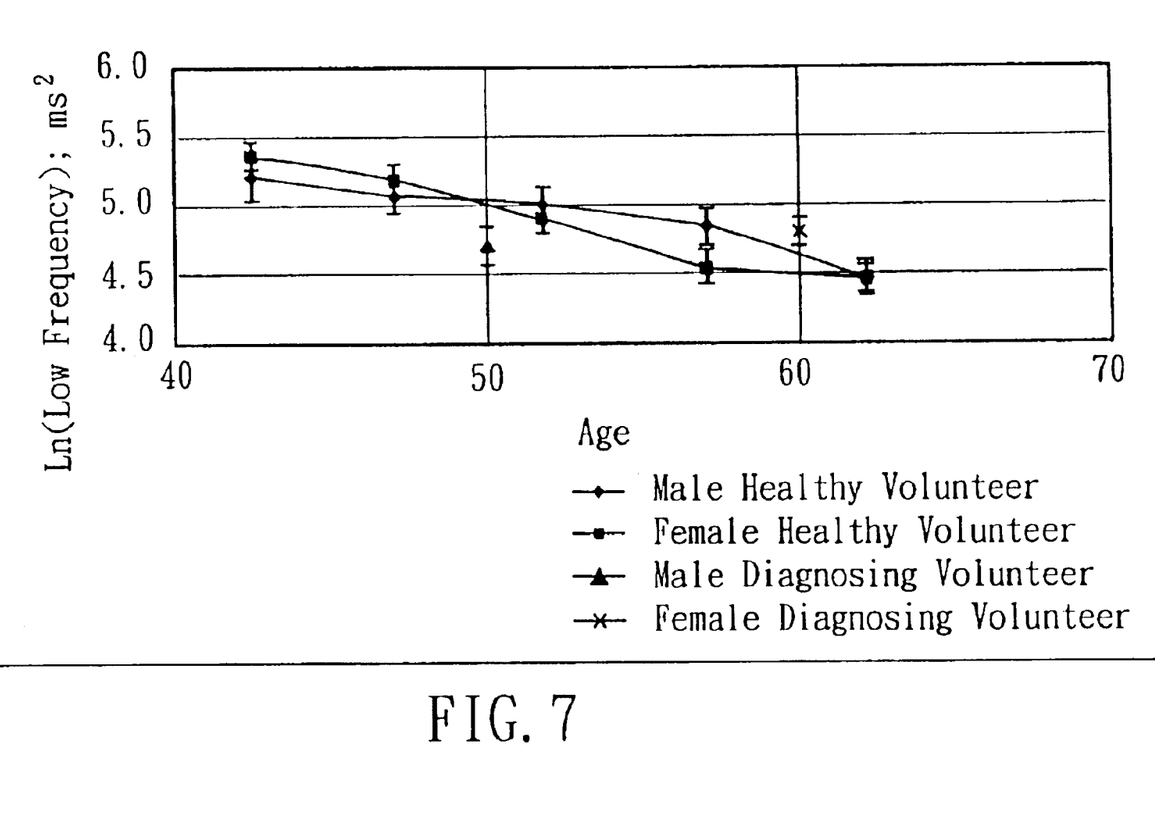
FIG. 7 illustrates the relations between the low frequency variability and the age of the control group and the experiment group.
Figure 8:
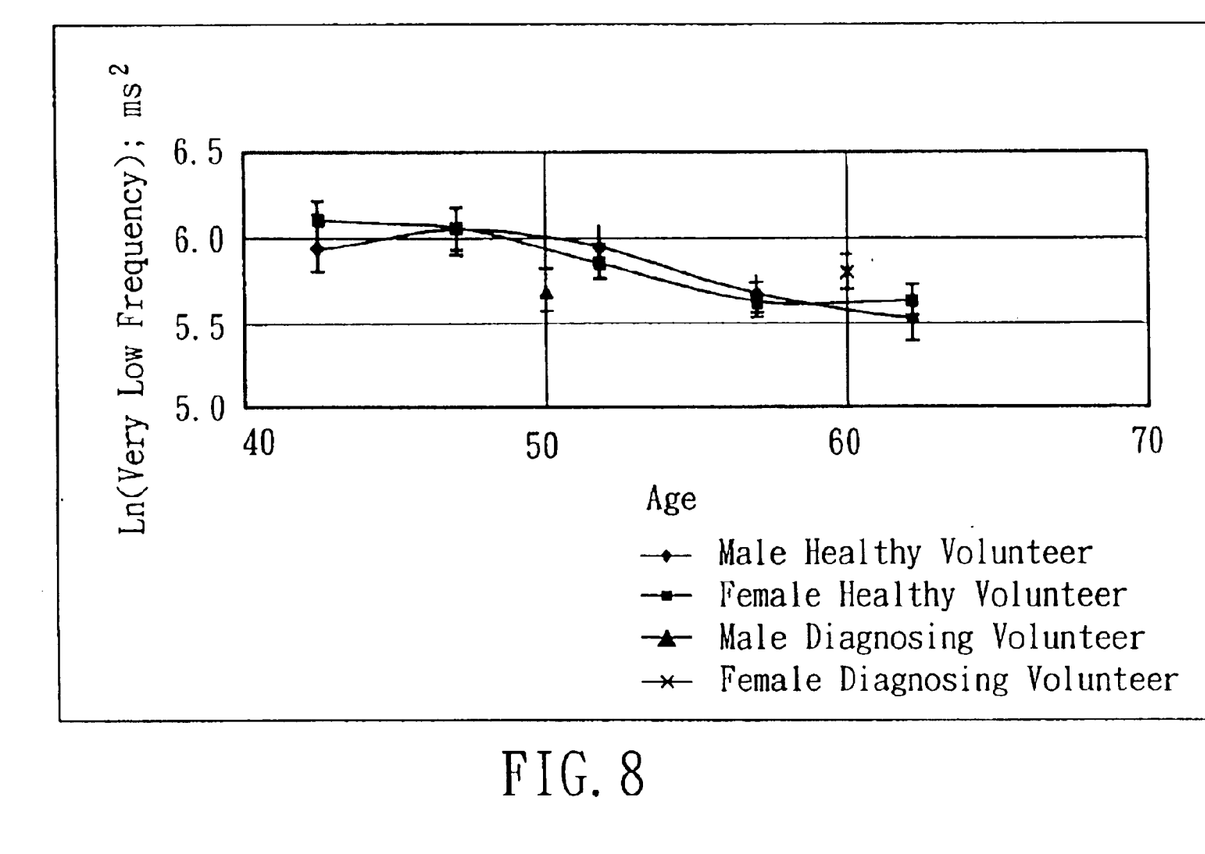
FIG. 8 illustrates the relations between the very low frequency variability and the age of the control group and the experiment group.

EXAMPLE 2
Monitoring Autonomic Nervous System Functional Change Side Effects Caused by Drugs in Human In this human experiment, the non-invasive apparatus system of the invention was used to monitor the autonomic nervous system functional change side effects caused by drugs. Four (two females and two males) apoplectic patients complicated with hypertension at the age of 77.3±8.8 (±means standard deviation) were chosen in the study. The patients were divided into two groups: (1) the control group and (2) the labetalol group (the experiment group). All patients, 5 minutes before administrating the drug, were classified as the control group. After being treated/injected with labetalol (12.5 mg) for 5 minutes, the patients became the labetalol group. Labetalol is an $\alpha$ and $\beta$ combined epinephrine antagonist (a sympathetic hormone epinephrine blocker) for lowering blood pressure. Treatment and analysis of the electrocardiograph (ECG) were conducted similarly to those recited in Example 1, except that the ranges of the frequencies were determined based on those of humans. The power of each frequency range comprising variance, low frequency power (0.04–0.15 Hz) and high frequency power (0.15–0.4 Hz) was quantified by integration. Parameters of the ratios of low frequency/high frequency (LF/HF ratio) and low frequency rate (LF%) were also calculated at the same time. The values of variance, LF, HF and LF/HF were logarithmically transformed to correct the distribution bias. All data were presented as mean±SD, and the differences between the experimental and control groups were examined by paired t-test, wherein a value of p<0.05 is considered as the data having a statistic meaning. FIG. 4 shows that when labetalol was administered, the heart rate period increased (i.e. decreasing the heart rate; p<0.05) and LF % and LF/HF (indexes of heart sympathetic nervous activity) decreased (p<0.05). Variance and HF responses were uncertain (P>0.05). In light of the results of the experiment, it has been proven that non-invasive apparatus system of the invention can be used in patients for monitoring autonomic nervous system functional change side effects caused by drugs.

EXAMPLE 3
Monitoring Aging of Sympathetic Nervous System in Human

In this human experiment, it will be shown that heart rate variability can be used as an index of aging of human autonomic nervous system, and based on the index, can be used in diagnosing aging and tracing the therapeutic effect to aging. A control group having 40 male and 40 female healthy volunteers and an aging diagnosis group having one male and one female volunteers were examined in this experiment. Any volunteers having hypertension, hypotension or cardiopathy were excluded from the control group. In the aging diagnosis group, the male volunteer (50 years old) had reported that he often felt dizziness before the experiment, and the female volunteer (60 years old) was more vital than those at the same age. All volunteers were instructed to lie down for ten minutes before being examined, and then the electrocardiographs (ECG) of the volunteers were recorded for five minutes. The electrocardiographs were measured by an 8-bit analog-digital converter with a catching frequency of 256 Hz. All peaks and mean intervals of heart rate period were monitored according to a standard procedure of electrocardiograph QRS complex by a computer analyzer. Furthermore, the spectral analysis was analyzed by the Fast Fourier Transform method. In the experiment, high frequency was defined as 0.15 to 0.40 Hz; low frequency was 0.04 to 0.15 Hz; and very low frequency was 0.003 to 0.04 Hz. Values of original mean intervals of heart rate period were filtered by an analyzing program to calculate the power spectral density of each element. The power $(ms)^2$ of each element was determined by integrating the value obtained from each frequency range, and the variance was calculated by integrating the whole frequency range. In the control group, the volunteers were further divided into four age groups of 40 to 44, 50 to 55, 55 to 59, and 60 to 64. In each group, the means and standard deviations (both presented as natural logarithm, Ln) of heart rate variability parameters were calculated. The heart rate variability parameters of the volunteers (one 50-year-old male and one 60-year-old female) of the aging diagnosis group were compared with those of the control group, and the results are shown in FIGS. 5 to 8. The results show that the variance, high frequency, low frequency and very low frequency in the control group (normal volunteers) decreased along with the increase of age, so that the heart rate variability parameters are highly associated with the age. In addition, in the aging diagnosis group, the parameters (variance, high frequency, low frequency and very low frequency) of the male volunteer (50-years-old) were all lower than those of normal 50-year-old males, which represents that his physiological age was older than his actual or chronological age. On the other hand, the parameters of the female volunteer (60-years-old) were all higher than those of normal 60-year-old females, which represents that her physiological age was younger than her actual age. Furthermore, as shown in FIGS. 5 to 8, the degree of aging is indeed different between males and females, which suggests that the diagnosis and the tracing of the therapeutic effect of aging should be varied depending on the patient's sex.

While the embodiments of the present invention have been illustrated and described, various modifications and improvements can be made by persons skilled in the art. The embodiments of the present invention are therefore described as an illustration but not in restrictive sense. It is intended that the present invention is not limited to the particular forms as illustrated, and that all the modifications departing from the spirit and scope of the present invention are within the scope as defined in the appended claims.

What is claimed is:

1. A non-invasive apparatus system to monitor the autonomic nervous system comprising:
   (a) a sensor for measuring artery sphygmograms or heart potential signals to form electric waves representing the artery sphygmograms or heart potential signals; and
   (b) an analyzer for receiving the electric waves from said sensor, wherein heart rate variability parameters in the electric waves are calculated by Fourier Transform or Fast Fourier Transform methods and spectral analysis; wherein said analyzer calculates the degree of the functional changed side effects caused by drugs, to monitor aging of the autonomic nervous system and tracing therapeutic effect thereof, based on said heart rate variability parameters.

2. The apparatus system according to claim 1, wherein the autonomic nervous functional change side effects and the aging of autonomic nervous system comprise the syndromes comprising hypertension, hypotension, arrhythmia, insomnia, unregulated body temperature, blushing, dizziness, or sweating.

3. The apparatus system according to claim 1, wherein the sensor is a pressure sensory device or one or more electrode chips.

4. The apparatus system according to claim 3, wherein the pressure sensory device is an apparatus worn on the wrist to measure the sphygmogram of a radial artery.

5. The apparatus system according to claim 1, wherein the heart rate variability parameters are selected from groups consisting of heart rate period, variance, total power, very low frequency variability, low frequency variability, high frequency variability, low frequency variability/high frequency variability, percentage of low frequency variability, and percentage of high frequency variability.

6. The apparatus system according to claim 1, wherein the analyzer further comprises a display device for showing the analyzing data and results recorded in the analyzer.

7. The apparatus system according to claim 1, wherein the analyzer comprises a warning device for emitting warning signals.

8. The apparatus system according to claim 1, wherein the analyzer further comprises an apparatus, which can transfer the measured and analyzed data to a terminal at hospitals or doctor's end, and the apparatus can further receive the signals transferred from the hospital or doctor.

9. The apparatus system according to claim 8, wherein the signal is transmitted by a wire or transmitted wirelessly.

10. A method for monitoring autonomic nervous system functional change side effects caused by drugs, which comprises the utilization of a non-invasive apparatus system in monitoring and calculating the heart rate variability parameters before and after taking the drug; wherein the value of change in the heart rate variability parameter being smaller than a predetermined value represents that the drug does not cause side effect to the autonomic nervous system, and the value of change in the heart rate variability parameter being between two predetermined values represents that the drug has induced a certain degree of functional change to the autonomic nervous system, and the value of change in the heart rate variability parameter being greater than a predetermined value represents that the drug has induced severe functional change to the autonomic nervous system; and the non-invasive apparatus system includes:
   (a) a sensor for measuring artery sphygmograms or heart potential signals to form electric waves representing the artery sphygmograms or heart potential signals; and
   (b) an analyzer for receiving the electric waves from said sensor, wherein heart rate variability parameters in the electric waves are calculated by Fourier Transform or Fast Fourier Transform method and spectral analysis.

11. A method for monitoring aging of autonomic nervous system and tracing therapeutic effect thereof, which comprises the utilization of a non-invasive apparatus system in monitoring and calculating the heart rate variability parameters, and the comparison of the parameters with those of normal people at the same age and sex; wherein the non-invasive apparatus system includes:
   (a) a sensor for measuring artery sphygmograms or heart potential signals to form electric waves representing the artery sphygmograms or heart potential signals: and
   (b) an analyzer for receiving the electric waves from said sensor, wherein heart rate variability parameters in the electric waves are calculated by Fourier Transform or Fast Fourier Transform method and spectral analysis.

* * * * *

UNITED STATES PATENT AND TRADEMARK OFFICE
CERTIFICATE OF CORRECTION

PATENT NO. : 6,811,536 B2
DATED : November 2, 2004
INVENTOR(S) : Dehchuan Sun et al.

It is certified that error appears in the above-identified patent and that said Letters Patent is hereby corrected as shown below:

Title page,
Item [73], Assignee, after "(TW)" add -- and Terry B. J. Kuo, Hualian (TW) --; and
Item [30], Foreign Application Priority Data, "CN" should read -- TW --.

Signed and Sealed this

Twenty-second Day of February, 2005

JON W. DUDAS
*Director of the United States Patent and Trademark Office*